United States Patent [19]

Scholl et al.

[11] Patent Number: 5,386,054
[45] Date of Patent: Jan. 31, 1995

[54] PROCESS FOR THE PURIFICATION OF POLYISOCYANATES, THE POLYISOCYANATES THUS PURIFIED AND USE THEREOF

[75] Inventors: Hans J. Scholl, Cologne; Hanns-Peter Müller, Odenthal; Rainer Welte, Leverkusen, all of Germany

[73] Assignee: Bayer Aktiengesellschaft, Leverkusen, Germany

[21] Appl. No.: 916,773

[22] Filed: Jul. 17, 1992

[30] Foreign Application Priority Data

Jul. 23, 1991 [DE] Germany .................. 4124318

[51] Int. Cl.$^6$ ......................... C07C 263/18
[52] U.S. Cl. ................... 560/352; 560/359; 521/154; 521/160; 528/67; 203/73
[58] Field of Search ........... 560/352, 359; 521/154, 521/160; 528/67; 203/73

[56] References Cited

U.S. PATENT DOCUMENTS

| 3,219,678 | 11/1965 | Kober et al. | 560/352 |
| 4,189,354 | 2/1980 | Ellendt et al. | 203/81 |
| 4,293,680 | 10/1981 | Mazanek et al. | 528/67 |
| 4,904,704 | 2/1990 | Nafziger et al. | 521/156 |
| 5,136,087 | 8/1992 | Van Horn et al. | 560/352 |

FOREIGN PATENT DOCUMENTS

| 1232134 | 1/1967 | Germany . |
| 1080717 | 8/1967 | United Kingdom . |
| 2207671 | 2/1989 | United Kingdom . |

OTHER PUBLICATIONS

*Patent Abstracts of Japan*, vol. 6, No. 165 (C-121)(1043), Aug. 28, 1982 JP-A-57 082 358, May 22, 1982.
*Chem. Abstracts*, vol. 114, No. 14, Apr. 8, 1991, Abstract No. 124644E & JP-A-2 140 277, May 29, 1990.
*Chem. Soc. Rev.* 3 (1974), pp. 209 to 230.

*Primary Examiner*—José G. Dees
*Assistant Examiner*—Joseph M. Conrad
*Attorney, Agent, or Firm*—Joseph C. Gil; N. Denise Brown

[57] ABSTRACT

A process for the purification of organic polyisocyanates by mixing of the polyisocyanate with from 0.001 to 1% by weight of compounds containing trimethylsilyl groups at temperatures of from 20° to 150° C. The resultant mixture of organic polyisocyanates and compounds containing trimethylsilyl groups is optionally treated by degasification or distillation. These purified polyisocyanates are suitable for the production of polyurethane plastics, and in particular, polyurethane foams.

3 Claims, No Drawings

PROCESS FOR THE PURIFICATION OF POLYISOCYANATES, THE POLYISOCYANATES THUS PURIFIED AND USE THEREOF

BACKGROUND OF THE INVENTION

This invention relates to a new process for the purification of organic polyisocyanates by mixing the polyisocyanates with certain silylated compounds. The resultant mixtures are optionally treated by degasification or worked up by distillation. These purified polyisocyanates are suitable for use in the production of polyurethane resins, and in particular, polyurethane foams.

There are various types and quantities of impurities present in polyisocyanates as a result of the production process which cause variations in activity of the polyisocyanates. The effects of these variations in activity of the polyisocyanates can be manifested in the products subsequently obtained from them, thus making reproducible and economical use of polyisocyanates difficult. In particular, the known phosgenation products of aniline/formaldehyde condensates, i.e. crude polyisocyanate mixtures of the diphenylmethane series, contain numerous such impurities. According to Chem. Soc. Rev. 3 (1974), pages 209 et seq, these are mainly impurities containing chlorine, which always give rise to fluctuations in activity if the chlorine is "highly mobile", i.e. a so-called hydrolyzable chlorine. Therefore, a reduction in the range of fluctuations in activity by reducing the quantity of these impurities so that the activity can be standardized and improved is technologically and economically important.

According to British Patent 1,080,717, the amount of hydrolyzable chlorine (HC value) can be reduced by a heat treatment at temperatures of from 180° to 220° C. Aside from the large consumption of energy required, such high temperature processes are dangerous due to the extremely high reactivity of polyisocyanates, which are liable to undergo oligomerization with a sudden release of heat.

It was therefore an object of the present invention to provide a new process for the purification of organic polyisocyanates which overcomes the above-mentioned disadvantages.

DESCRIPTION OF THE INVENTION

The above noted problem has been solved by the process according to the present invention. The principle of the process according to the invention resides in adding a small quantity of certain silylated compounds to the technical polyisocyanates to be treated, and, optionally, thereafter degasifying the resultant mixtures or working them up by distillation.

The present invention relates to a process for the purification of organic polyisocyanates, to the polyisocyanates purified by this process, and to the use of the thus purified polyisocyanates as a starting material for the production of polyurethane resins by the isocyanate polyaddition process, and in particular, for the production of polyurethane foams.

The present process for the purification of organic polyisocyanates is characterized in that the organic polyisocyanates are mixed at temperatures of from 20° to 150° C. with a total of from 0.001 to 1% by weight, based on the quantity of polyisocyanates, of compounds containing trimethylsilyl groups corresponding to formulas (Ia) and/or (Ib), and, optionally, formula (II):

The molar ratio of compounds (Ia) and/or (Ib) to compounds (II) is from 1:0 to 1:1, and in formula (II)
X represents the neutral acid group obtainable by removal of the acidic hydrogen atoms from an n-basic, oxygen-containing acid having a pKa-value of at most 2, and
n represents an integer of from 1 to 3.

The resultant mixture is optionally subjected to a degasification or distillative working up, after a dwell time of at least 5 minutes up to 180 minutes.

The starting material for the process according to the invention may be any organic polyisocyanate of the type known from polyurethane chemistry.

Suitable starting polyisocyanates include, for example, aliphatic and cycloaliphatic diisocyanates such as 1,6-diisocyanato-hexane (HDI), 1-isocyanato-3,3,5-trimethyl-5-isocyanato-methyl-cyclohexane (IPDI), 4,4'-diisocyanatodicyclohexylmethane (HMDI) and any mixtures of such diisocyanates. Aromatic diisocyanates such as 2,4- and/or 2,6-diisocyanatotoluene (TDI) may also be used as starting materials according to the invention. Any modified polyisocyanate may also be used as a starting material according to the invention. Reaction mixtures such as those obtained from the trimerization of a proportion of the isocyanate groups of HDI, IPDI or mixtures of HDI and IPDI for the production of the corresponding polyisocyanates containing isocyanurate groups are of particular interest. These reaction mixtures consist substantially of the above-mentioned starting diisocyanates and the resulting polyisocyanates containing isocyanurate groups.

It is particularly preferred for the process according to the invention to use polyisocyanates or polyisocyanate mixtures of the diphenylmethane series, including those which are chemically modified.

These include, for example, the crude phosgenation products of aniline/formaldehyde condensates ("crude MDI") and distillation fractions obtained from these crude mixtures, for example, polyisocyanates or polyisocyanate mixtures consisting of 80 to 100% by weight of diisocyanatodiphenylmethane isomers and 0 to 20% by weight of higher than difunctional polyisocyanates of the diphenylmethane series. The diisocyanatodiphenylmethane isomers generally contain from 40 to 100% by weight, and preferably from 40 to 80% by weight, of 4,4'- diisocyanatodiphenylmethane, with the remainder being composed of 2,4'-diisocyanatodiphenylmethane and, optionally, 2,2'-diisocyanatodiphenylmethane. The amount of the 2,2'-diisocyanatodiphenylmethane used may be up to 8% by weight, based on the weight of the diisocyanates.

The above-mentioned polyisocyanates or polyisocyanate mixtures may also be used in a chemically modified form. By chemical modification is meant, in particular, urethanization, carbodiimidization, dimerization or trimerization of a proportion of the isocyanate groups. Suitable urethanized starting compounds are, in particular, reaction products of the polyisocyanates or polyisocyanate mixtures exemplified above with subequivalent quantities of polyhydric alcohols, in particular, with polypropylene glycols having a molecular weight of at most 700, in which an NCO/OH equivalent ratio of from 10:1 to 10:3 is maintained. Suitable products of carbodiimidization are, in particular, derivatives of the above exemplified polyisocyanates or polyisocyanate mixtures containing carbodiimide groups and/or uretoneimine groups, prepared in known manner by the carbodiimidization of from 5 to 30% by weight of the isocyanate groups with the aid of carbodiimidization catalysts. Examples of suitable dimerization and/or trimerization products include derivatives of the above exemplified polyisocyanates or polyisocyanate mixtures containing uretdione and/or isocyanurate groups, prepared by dimerization and/or trimerization with uretdione and/or isocyanurate formation of from 10 to 30% of the isocyanate groups, using known trimerization catalysts. Any mixtures of the chemically modified polyisocyanates or polyisocyanate mixtures may, of course, also be used.

Crude polyisocyanate mixtures of the diphenylmethane series having viscosities of from 10 to 800 at 24° C., preferably of from 15 to 400, are particularly preferred for the process according to the invention. These polyisocyanate mixtures generally have a hydrolyzable chlorine content (HC value) of from 0.01 to 0.2% by weight, and preferably of from 0.02 to 0.1% by weight.

To carry out the process according to the invention, a total of from 0.001 to 1.0% by weight, preferably of from 0.01 to 0.3% by weight, based on the polyisocyanate, of certain compounds containing trimethylsilyl groups are added to the starting polyisocyanates. The optimum quantity of these silyl-containing compounds can easily be determined by a preliminary investigative test. These compounds are added within the temperature range of from 20° to 150° C., and preferably of from 50° to 120° C.

The trimethylsilyl group-containing compounds to be added are compounds corresponding to formulas (Ia) and/or (Ib) shown below, and, optionally, formula (II). The molar ratio of compounds (Ia) and/or (Ib) to compound (II) is from 1:0 to 1:1.

(CH$_3$)$_3$Si—NH—Si(CH$_3$)$_3$      (Ia)

(CH$_3$)$_3$Si—NH—CO—NH—Si(CH$_3$)$_3$      (Ib)

X—[Si(CH$_3$)$_3$]$_n$      (II).

In formula (II),
X represents the neutral acid group obtained by removal of the acidic hydrogen atoms from an n-basic, oxygen-containing acid having a pKa-value of at most 2, and
n represents an integer from 1 to 3.

Examples of silylated oxyacids corresponding to formula (II) include silylated sulphonic acids such as trifluoromethane sulphonic acid trimethyl silyl ester or methane sulphonic acid trimethyl silyl ester, silylated esters of acids of phosphorus such as phosphoric acid tris-(trimethyl silyl ester) or phosphoric acid diethyl ester-trimethyl silyl ester.

The mixture of polyisocyanate and silylated compounds (Ia) and/or (Ib) and, optionally, (II) is preferably subjected to degasification under vacuum (for example at 1 to 100 mbar) or distillative working up, after a period of at least 5 minutes, and preferably at least 30 minutes, during which the mixture is kept at 20° to 150° C., and preferably at 50° to 120° C. When starting isocyanates capable of being distilled are used, this distillative working up means their preparation in a pure form by distillation, for example, in a thin layer evaporator.

Polyisocyanates which have been treated according to the invention have comparatively low fluctuations in activity. This can be easily confirmed from the reduced HC-values, which are an indication of improved activity with comparable foaming. The following examples of execution illustrate the invention. The "HC-values" given are based on the hydrolyzable chlorine content. All percentages given are based on weight.

EXAMPLES

Starting Polyisocyanates

Polyisocyanate 1

Crude polyisocyanate mixture of the diphenylmethane series having an NCO content of 30.9%, a viscosity at 24° C. of 200 mPa.s and an HC-value of 0.088%.

Polyisocyanate 2

Crude polyisocyanate mixture of the diphenylmethane series having an NCO content of 31.2%, a viscosity at 24° C. of 100 mPa.s and an HC-value of 0.068%.

Polyisocyanate 3

Polyisocyanate mixture of the diphenylmethane series having an isocyanate content of 32.2%, a viscosity at 24° C. of 25, mPa.s and an HC-value of 0.027%, consisting of
59% of 4,4'-diisocyanatodiphenylmethane
23% of 2,4'-diisocyanatodiphenylmethane,
3% of 2,2'-diisocyanatodiphenylmethane and
15% of higher homologues.

Polyisocyanate 4

Polyisocyanate mixture of the diphenylmethane series having an isocyanate content of 32.4%, a viscosity at 24° C. of 20, mPa.s and an HC-value of 0.082%, consisting of
56% of 4,4'-disocyanatodiphenylmethane,
29% of 2,4'-diisocyanatodiphenylmethane,
5% of 2,2'-diisocyanatodiphenylmethane and
10% of higher homologues.

Example 1 (Process According to the Invention)

1 kg of Polyisocyanate 1 is heated to 90° C. under nitrogen with stirring and 1 g of hexamethyldisilazane of formula (Ia) (HMDS) and 0.1 g of phosphoric acid-tris-(trimethylsilyl ester) (PSTMS) are added. The reaction mixture is then stirred for 2 hours at 90° C. and briefly degasified in a water jet vacuum (30 mbar, 10 min.). An isocyanate mixture according to the invention having a reduced HC-value of 0.073% is obtained after cooling. The isocyanate content and viscosity are unchanged.

Example 1 a (Comparison Example)

Example 1 is repeated without the addition of HMDS and PSTMS. The isocyanate content and viscosity are unchanged and the HC-value is 0.087%.

Foaming of the isocyanate mixture from Examples 1 and 1a using a conventional rigid foam formulation indicates comparative improvement in the activity of the polyisocyanate mixture which has been purified according to the invention. The cream time of the foam mixture is reduced from 39 to 31 seconds (Table 1).

TABLE 1

| Polyol 1 | 52 weight-% | 52 weight-% |
|---|---|---|
| Polyol 2 | 35 weight-% | 35 weight-% |
| Flame Retardant | 13 weight-% | 13 weight-% |
| Catalyst | 1.3 | 1.3 |
| Stabiliser | 1.2 | 1.2 |
| R 11 (CCl$_3$F) | 26 weight-% | 26 weight-% |
| Water | 0.5 | 0.5 |
| Polyisocyanate [Example 1] | 133 weight-% | — |
| Polyisocyanate [Example 1a] | | 133 weight-% |
| Mixing time | 10 seconds | 10 seconds |
| Cream time | 31 seconds | 39 seconds |

Polyol 1: Polypropylene oxide ether, OH value 470,
starter: sugar 81% OH
propylene glycol 14% OH
water 5% OH
Polyol 2: Polypropylene oxide ether, OH value 450,
starter: sugar 38% OH
ethylene glycol 61% OH
water 1% OH
Flame Retardant: Aminophosphono acid ester, OH value 450
Catalyst: N,N'-dimethyl cyclohexylamine
Stabiliser: Polyether siloxane B 8421, a product of Goldschmidt. Essen.

Examples 2 to 6 carried out similarly are summarized in Table 2:

TABLE 2

| Examples | 2 | 3 | 4 | 5 | 6 | 7 | 8 | 9 |
|---|---|---|---|---|---|---|---|---|
| Starting product | Polyisocyanate 1 (1000 g) | Polyisocyanate 2 (1000 g) | Polyisocyanate 3 (1000 g) | Polyisocyanate 4 (1000 g) | Polyisocyanate 1 (1000 g) | Polyisocyanate 1 (1000 g) | Polyisocyanate 4 (1000 g) | Polyisocyanate 2 (1000 g) |
| N-silyl compound | HMDS (1 g) | HMDS (1 g) | HMDS (1 g) | HMDS (1 g) | HMDS (1 g) | BSU (1.3 g) | BSU (1.3 g) | BSU (0.6 g) HMDS (0.5 g) |
| Silylated acid | TRIF (0.2 g) | PSTMS (0.2 g) | PSTMS (0.1 g) | PSTMS (0.1 g) | — | PSTMS (0.1 g) | PSTMS (0.1 g) | PSTMS (0.1 g) |
| Temperature | 90° C. | 90° C. | 90° C. | 90° C. | 90° C. | 90° C. | 90° C. | 90° C. |
| Time | 2 hours | 2 hours | 2 hours | 2 hours | 2 hours | 2 hours | 2 hours | 1 ½ hours |
| HC-value | 0.074% | 0.058% | 0.022% | 0.064% | 0.077% | 0.075% | 0.070% | 0.057% |

HMDS: Hexamethyldisilazane
TRIF: Trifluoromethane sulphonic acid trimethyl silyl ester
PSTMS: Phosphoric acid tris-(trimethylsilyl ester)
BSU: N,N'-Bis-(trimethyl silyl)-urea

What is claimed is:

1. A process for the purification of organic polyisocyanates, comprising mixing
   A) organic polyisocyanates at temperatures of from 20° to 150° C., with
   B) a total of from 0.001 to 1% by weight, based on the quantity of polyisocyanates, of compounds containing trimethyl silyl groups corresponding to the formulae (Ia) and/or (Ib), and (II)

$$(CH_3)_3Si-NH-Si(CH_3)_3 \quad (Ia)$$

$$(CH_3)_3Si-NH-CO-NH-Si(CH_3)_3 \quad (Ib)$$

$$X-[Si(CH_3)_3]_n \quad (II),$$

wherein the molar ratio of compounds (Ia) and/or (Ib) to compounds of formula (II) is from 1:0 to 1:1, and in formula (II)

X represents the neutral acid group as obtained by removal of the acidic hydrogen atoms from an n-basic, oxygen-containing acid having a pKa-value of at most 2, and n represents an integer from 1 to 3;

and separating the resultant mixture of organic polyisocyanates and compounds containing trimethy silyl groups by either
   1) degasification under vacuum, or
   2) distillative working up,
after a dwell time of at least 5 minutes, during which time the mixture is kept at temperatures of from 20° to 150° C.

2. The process of claim 1, wherein said polyisocyanates are polyisocyanates of the diphenylmethane series, chemically modified polyisocyanates of the diphenylmethane series, or mixtures thereof.

3. The process of claim 1, wherein said compounds containing trimethyl silyl groups corresponding to formula (II) are selected from the group consisting of trifluoromethane sulphonic acid trimethyl silyl ester and phosphoric acid tris-(trimethyl silyl ester).

* * * * *